United States Patent [19]

Tahara et al.

[11] Patent Number: 4,617,314
[45] Date of Patent: Oct. 14, 1986

[54] BENZOFURAN- AND BENZOPYRAN-CARBOXAMIDE DERIVATIVES

[75] Inventors: Tetsuya Tahara, Nakatsu; Kiyoharu Hayano, Fukuoka; Michihide Setoguchi, Nakatsu; Takemi Fukuda, Fukuoka, all of Japan

[73] Assignee: Yoshitomi Pharmaceutical Industries Ltd., Osaka, Japan

[21] Appl. No.: 591,363

[22] Filed: Mar. 20, 1984

[30] Foreign Application Priority Data

Apr. 8, 1983 [JP] Japan .................................. 58-62554

[51] Int. Cl.$^4$ ..................... A61K 31/34; A61K 31/35; C07D 405/12
[52] U.S. Cl. .................................... 514/422; 514/466; 514/456; 514/465; 514/316; 514/320; 514/228; 514/229; 514/232; 514/234; 548/525; 548/518; 548/523; 549/404; 549/405; 549/467; 549/462; 546/196; 546/187; 544/151; 544/153; 544/79; 544/129; 544/142
[58] Field of Search ........................ 548/525, 518, 523; 549/404, 405, 467, 462; 546/196, 187; 544/151, 153, 79, 129, 142; 514/422, 466, 456, 465, 316, 320, 228, 229, 232, 234

[56] References Cited

U.S. PATENT DOCUMENTS

| | | | |
|---|---|---|---|
| 3,177,252 | 4/1965 | Thominet et al. | 564/167 |
| 3,342,826 | 9/1967 | Miller et al. | 546/224 |
| 3,745,175 | 7/1973 | Thominet et al. | 548/525 |
| 3,849,417 | 11/1974 | Hubner et al. | 544/297 |
| 3,860,619 | 1/1975 | Christensen et al. | 424/285 X |
| 3,953,462 | 4/1976 | Gruber et al. | 546/269 |
| 4,205,080 | 5/1980 | Carr | 424/285 X |
| 4,525,356 | 6/1985 | Itho et al. | 514/456 X |

FOREIGN PATENT DOCUMENTS 1358684 7/1974 United Kingdom .

OTHER PUBLICATIONS

Christensen et al.; Chem. Abstracts; vol. 76 (1972), entry 99520y.
European Search Report for EP 84103843.3.

Primary Examiner—Donald G. Daus
Assistant Examiner—William A. Teoli, Jr.
Attorney, Agent, or Firm—Armstrong, Nikaido, Marmelstein & Kubovcik

[57] ABSTRACT

Benzofuran- and benzopyran-carboxamide derivatives of the formula:

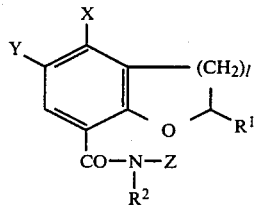

wherein $l$ is 1 or 2; X is hydrogen atom, amino group or halogen atom; Y is $-S(O)_m-R^3$ wherein $R^3$ is lower alkyl group and m is 0, 1 or 2, or

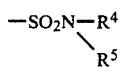

wherein $R^4$ and $R^5$ are the same or different and are each hydrogen atom or lower alkyl group; $R^1$ is hydrogen atom, lower alkyl group, arylthiomethyl group, halogenomethyl group or

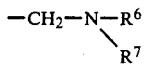

wherein $R^6$ and $R^7$ are the same or different and are each hydrogen atom or lower alkyl group or $R^6$ and $R^7$ together with the adjacent nitrogen atom form a hetrocycle; $R^2$ is hydrogen atom or lower alkyl group; and Z is

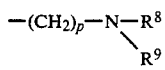

wherein p is 2 or 3, $R^8$ and $R^9$ are the same or different and are each lower alkyl group or $R^8$ and $R^9$ together with the adjacent nitrogen atom form a heterocycle, or

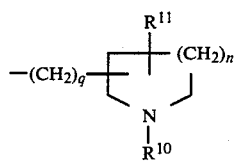

wherein q is 0 or 1, n is 1 or 2, $R^{10}$ is lower alkyl group, lower alkenyl group, lower alkinyl group, aralkyl group or cycloalkyl group and $R^{11}$ is hydrogen atom or lower alkyl group, their physiologically acceptable salts or their optical isomers, and a method of preparing same. These compounds are useful as psychotropic and antipsychotic agents.

11 Claims, No Drawings

BENZOFURAN- AND BENZOPYRAN-CARBOXAMIDE DERIVATIVES

This invention relates to novel and pharmaceutically useful benzofuran- or benzopyran-carboxamide derivatives represented by the formula:

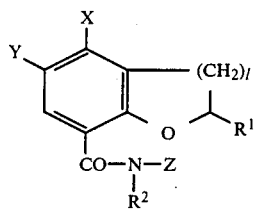

(I)

wherein l is 1 or 2; X is hydrogen atom, amino group or halogen atom; Y is $-S(O)_m-R^3$ ($R^3$ is lower alkyl group and m is 0, 1 or 2) or

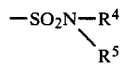

($R^4$ and $R^5$ are the same or different and each is hydrogen atom or lower alkyl group); $R^1$ is hydrogen atom, lower alkyl group, arylthiomethyl group, halogenomethyl group or

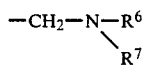

($R^6$ and $R^7$ are the same or different and each is hydrogen atom or lower alkyl group or $R^6$ and $R^7$ together with the adjacent nitrogen atom form a heterocycle); $R^2$ is hydrogen atom or lower alkyl group; Z is

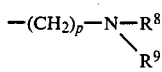

(p is 2 or 3 and $R^8$ and $R^9$ are the same or different and each is lower alkyl group or $R^8$ and $R^9$ together with the adjacent nitrogen atom form a heterocycle) or

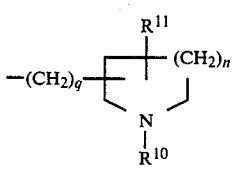

(q is 0 or 1, n is 1 or 2, $R^{10}$ is lower alkyl group, lower alkenyl group, lower alkinyl (alkynal) group, aralkyl group or cycloalkyl group and $R^{11}$ is hydrogen atom or lower alkyl group), their salts and their optical isomers.

More specifically stated with the aforementioned generic formula, the lower alkyl group includes, e.g. methyl, ethyl, propyl, isopropyl, butyl, tert-butyl, etc.; the halogen atom includes, e.g. fluorine, chlorine, bromine, etc.; the arylthiomethyl group includes, e.g. phenylthiomethyl; the halogenomethyl group includes, e.g. chloromethyl, bromomethyl, iodomethyl, etc.; the heterocycle includes, e.g. 1-pyrrolidinyl, piperidino, morpholino, 4-methyl-1-piperidinyl, etc.; the lower alkenyl group includes, e.g. allyl, 2-butenyl, etc.; the lower alkinyl group includes, e.g. propargyl, etc.; the aralkyl group includes, e.g. benzyl, phenethyl, etc. which may be substituted by lower alkyl, lower alkoxy, halogen, etc.; and the cycloalkyl group includes, e.g. cyclohexyl, etc.

It is an object of this invention to provide the compounds of the foregoing generic formula (I) which are useful for therapeutic treatment of psychosomatic diseases and psychic disturbances or mental disorders.

Recently, sulpyride represented by the formula:

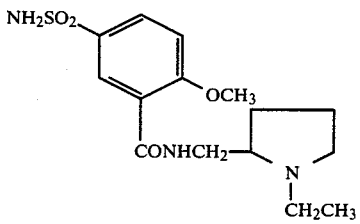

has been known to have anti-schizophrenic actions as well as anti-ulcer actions. The sulpyride as a psychotropic agent is reported to have less side effects on the extrapyramidal system and weak cataleptogenic activity, as opposed to existing drugs of this kind such as butyrophenone-series compounds, e.g. haloperidol or phenothiazine-series compounds, e.g. chlorpromazine. This suggests that sulpyride has more selectivity to the dopamine antagonistic action in the mesolimbic system rather than the dopamine neuron blockade in the negrostriatum.

On the other hand, sulpyride is also known to have a low uptake rate in living organisms upon oral administration and be difficult to cross blood-brain barrier.

With the foregoing problems in view, the present inventors have investigated a series of new benzofuran- or benzopyran-carboxamides. As a result, this invention has been accomplished by finding such compounds that have excellent oral uptake and blood-brain barrier permeability, anti-dopamine action having higher affinity to the mesolimbic system, potent methamphetamine potentiation, potent antiemetic action, and low toxicity.

Thus, the compounds of this invention are useful as a medicament for psychosomatic diseases such as gastric ulcer, duodenal ulcer, etc. or for suppression of vomiting or as a therapeutical agent for psychic disturbances and mental disorders such as schizophrenia, depressive psychosis or anxiety, etc.

The compounds of Formula (I) with which this invention is concerned are produced by reacting a carboxylic acid of the general formula:

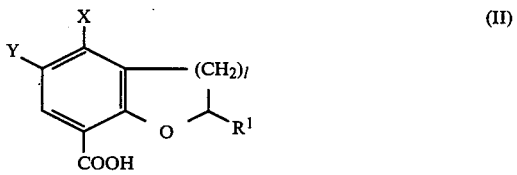

(II)

wherein the symbols are the same as defined above, or its reactive derivative and a compound of the formula:

(III)

wherein the symbols are the same as defined above.

(1) Where the compound (II) is a free carboxylic acid, the reaction is carried out in the presence of a condensation agent such as dicyclohexylcarbodiimide, tetrachlortitan, phosphorus halogenide (e.g. phosphorus trichloride, phosphorus oxychloride), diethylchlorphosphite, o-phenylenechlorphosphite, ethyldichlorphosphite, etc. in an inert solvent under cooling, at room temperature or under warming. It is also possible preliminarily to make a phosphorus halogenide to act on the compound (III) and then to make to condense with the compound (II). For instance, in case of phosphorus trichloride, beforehand, about ½ mol of phosphorus trichloride is made to act upon the compound (III) in an inert solvent in the presence of a tertiary amine such as triethylamine, pyridine, N,N-dimethylaniline, etc. under cooling or at room temperature and subsequently, the resulting product is made to react with the compound (II) in an inert solvent at room temperature or under warming, preferably under heating and reflux.

(2) Where the reactive derivative of the carboxylic acid of Formula (II) is an acid halide, e.g. acid chloride or acid bromide, the reaction is carried out in an inert solvent in the presence of a tertiary amine, e.g. triethylamine, pyridine, N,N-dimethylaniline under cooling or at room temperature or in the presence of alkali, e.g. sodium hydroxide, potassium hydroxide, etc. in water under cooling or at room temperature.

(3) Where the reactive derivative of the compound (II) is an acid azide, the reaction is carried out in the presence of alkali, e.g. sodium hydroxide, potassium hydroxide, etc. in water under cooling or at room temperature.

(4) Where the reactive derivative of the compound (II) is an ester derivative, e.g. methyl ester, ethyl ester, p-nitrophenyl ester, p-chlorophenyl ester, etc., the reaction is carried out in an inert solvent (excess amount of the compound (III) may be used so as to serve as a solvent as well) at room temperature or under warming, preferably under heating and reflux.

(5) Where the reactive derivative of the compound (II) is a symmetrical acid anhydride or mixed acid anhydride, e.g. mixed alkylcarbonic acid anhydride, mixed alkylphosphoric acid anhydride, mixed alkylphosphorous acid anhydride, mixed sulfuric acid anhydride, etc., the reaction is carried out in an inert solvent in the presence of a tertiary amine such as triethylamine, pyridine, N,N-dimethylaniline under colling, at room temperature or under warming.

(6) Where the reactive derivative of the compound (II) is an active amide, e.g. acid imidazolide, acid pyrrolizide, 2,4-dimethylpyrazolide, etc., the reaction is carried out in an inert solvent at room temperature or under warming.

The inert solvent to be used in the aforementioned condensation reactions includes for example, benzene, toluene, xylene, methanol, ethanol, isopropanol, ethyl ether, dioxane, tetrahydrofuran, chloroform, dichloromethane, dichloroethane, hexamethylphosphorictriamide, diethylene glycol, dimethylformamide, etc. singly or in combination and is chosen appropriately depending on the kind of the reactive derivatives.

Among the compounds of Formula (I) according to this invention, a group consisting of them wherein $R^1$ is not hydrogen and/or the radical of Z contains chiral carbon atoms is obtained as racemic mixtures. The present invention covers respective optically active isomers of the compounds (I), as well.

The racemic mixture, if desired, can be optically resolved in conventional manner with an optically active acid (e.g. tartaric acid, dibenzoyltartaric acid, mandelic acid, 10-camphorsulfonic acid) by availing itself of the basicity. It is also possible to prepare stereo-selectively the intended compounds (I) having desired steric configuration by subjecting an optically active carboxylic acid (II) or its reactive derivative obtained from a racemate (II) ($R^1 \neq H$) by the optical resolution of it with an optically active base (e.g. cinchonine, cinchonidine, brucine, quinine or α-methylbenzylamine, etc.) and an optically active compound (III) prepared by the resolution with an optically active acid (e.g. tartaric acid, dibenzoyltartaric acid, mandelic acid, 10-camphorsulfonic acid, etc.) to the condensation reaction.

The compounds of Formula (I) can be made into their acid addition salts physiologically acceptable, e.g. hydrochloride, hydrobromide, phosphate, fumarate, tartarate, sulfate, citrate, lactate, maleate, toluenesulfonate.

Good pharmacological actions the compounds of the invention exert will be hereinafter described.

Dopamine antagonism was observed by the antagonism to (1) hypermotility of mice, and
(2) stereotyped behavior of rats induced by the administration of apomorphine to the animals which drug acts on dopamine. The response of (1) is considered to be due to the action of dopamine on the mesolimbic system whereas the response of (2) is regarded mainly as the action of dopamine on the extrapyramidal system. As a consequence, a drug having high selectivity to the antagonism to the response of (1) is deemed to be more useful with less extrapyramidal side effects.

Activation effect was construed as lethality increasing effect of a test drug on rats which were administered with methamphetamine at a non-lethal dose every week. Accordingly, it is considered that the greater is the number of rats which died at a lower dose in an earlier week, the activation activity is the higher.

(1) Anti-apomorphine Action (mice)

Groups of 5 male dd-strain mice were used. Test compounds were orally administered and 60 minutes thereafter, 0.5 mg/kg of apomorphine hydrochloride was intracutaneously administered. Immediately thereafter, spontaneous motility of the mice was measured with the aid of Animex (manufactured by Columbus Company, U.S.A.) for 20 minutes. The procedure was repeated three times with respective groups. The dose of test compounds required for 50% suppression of spontaneous motility of control group was graphically intraporated and determined as $ED_{50}$ value. The results are shown in Table 1.

(2) Anti-apomorphine Action (rats)

Groups of 7 female Wistar rats were used. Test compounds were orally administered, 60 minutes thereafter, apomorphine hydrochloride was intravenously administered at a dosage of 1.25 mg/kg. After 5 minutes and 20 minutes, respectively, whether gnawing behavior (stereotyped behavior) appears or not during the period of 5 minutes was observed. The dose of test compounds required for 50% suppression of the appearance was evaluated as $ED_{50}$ value by probit method. The results are shown in Table 1.

(3) Methamphetamine Potentiation Action

Groups of 8 male Wistar rats weighing above 400 mg were used. Test compounds are intraperitoneally administered and 15 minutes thereafter, 5 mg/kg of methamphetamine hydrochloride was intraperitoneally administered. Number of dead rats within one week was counted. In the 2nd to 4th week, experiment was likewise repeated at one week intervals by the administration of test compounds and methamphetamine hydrochloride. The results are shown in Table 2.

TABLE 1

| Compound | Anti-apomorphine Action ED$_{50}$ (mg/kg, p.o.) | |
|---|---|---|
|  | (1) Mice, Motility | (2) Rats, Stereotyped Behavior |
| A | 80 | >100 |
| B | 23 |  |
| C | 85 |  |
| D | 6 | 21 |
| E | 100 | >100 |
| F | 17 | >100 |
| G | 35 | >100 |
| H | 19 | 60 |
| I | 30 | >100 |
| J | 10 | >100 |
| K | 0.65 | 0.20 |
| Sulpyride | 330 | >500 |

TABLE 2

| Compound and Dose (mg/kg, i.o.) | Methamphetamine Potentiation Action Number of Dead Animal, Total Number | | | |
|---|---|---|---|---|
|  | 1st Week | 2nd Week | 3rd Week | 4th Week |
| A    5 | 1 | 1 | 1 | 1 |
|     10 | 0 | 3 | 4 | 4 |
|     20 | 2 | 5 | 5 | 7 |
| F   10 | 0 | 0 | 0 | 1 |
|     25 | 0 | 0 | 1 | 2 |
|     50 | 0 | 2 | 3 | 6 |
| H   20 | 0 | 6 | 6 | 7 |
|     40 | 2 | 4 | 7 | 7 |
| L   25 | 3 | 3 | 7 | 8 |
| Sulpy- 20 | 0 | 0 | 0 | 0 |
| ride   40 | 0 | 0 | 1 | 1 |
|     80 | 2 | 3 | 3 | 3 |

Test Compounds

Test Compounds correspond to, as shown in Table 3 below, those of Examples which will be hereinafter described.

TABLE 3

| Compound | Example No. | Compound | Example No. |
|---|---|---|---|
| A | 1 | G | 47 |
| B | 2 | H | 7 |
| C | 3 | I | 8 |
| D | 6 | J | 9 |
| E | 20 | K | 10 |
| F | 23 | L | 22 |

The compounds of this invention, when used as medicaments, can be administered in the form of tablets, balls, capsules, powders, solutions or injectable solutions suitably in the combination with excipients, bulking agents, diluents, etc.

The following is an example of formulations when a compound of the invention is administered for therapeutical purposes:

Tablets (120 mg) are prepared from the ingredients:
Compound I(Example 8): 20 mg
D-Mannitol: 60 mg
Talc: 4 mg
Hydroxypropylmethyl Cellulose 2910: 5 mg
Titanium Oxide: 3 mg
Cornstarch: 28 mg The dose for adult human beings is usually in the range of 0.01–10 mg/kg per one dosage, but may vary depending on the compounds to be chosen, conditions of disease, age, etc.

The compounds of Formula (II) as the one starting material are novel. For instance, the starting material of the formula:

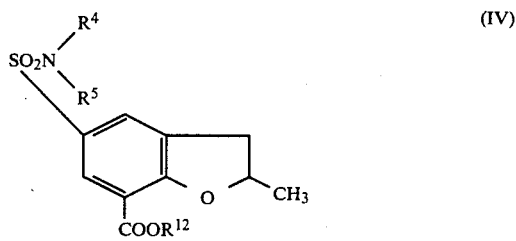
(IV)

wherein $R^4$ and $R^5$ are the same as defined above, and $R^{12}$ is hydrogen atom or lower alkyl group, is prepared by reacting a compound of the formula:

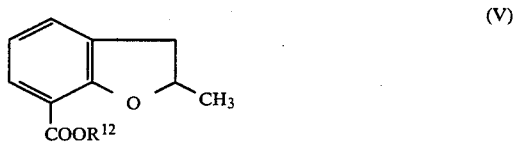
(V)

wherein $R^{12}$ is the same as defined above, and chlorosulfonic acid at 0°–70° C., preferably 0°–30° C. to produce a compound of the formula:

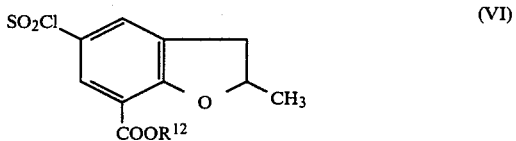
(VI)

wherein $R^{12}$ is the same as above, and subsequently by reacting the resulting product and a compound of the formula:

(VII)

wherein $R^4$ and $R^5$ are the same as defined above, at 0°–30° C.

The ester compounds (IV) thus obtained wherein $R^{12}$ is lower alkyl group can be converted into the carboxylic acids (IV) wherein $R^{12}$ is hydrogen by alkaline hydrolysis. Conversely, the carboxylic acids (IV) can be converted into the ester compounds (IV) by esterification with lower alkanol and acid catalyst.

Reference Example

2-Methyl-2,3-dihydrobenzofuran-7-carboxylic acid, 50 g, is incorporated little by little into 140 ml of chlorosulfonic acid under ice-cooling. After the addition, the whole is agitated under ice-cooling for 15 minutes followed by at room temperature for 15 hours. The reactant solution is portionwise incorporated with stirring into 1.5 l of ice water. Precipitated crystals are collected by suction filtration and washed with cold water three times. Immediately thereafter, the crystals are added with stirring to 250 ml of ammonia water, and stirring is conducted at room temperature for one hour. Excess ammonia is roughly distilled off under reduced pressure and concentrated hydrochloric acid is added with stirring to the resulting residue to render strongly acidic. Under ice-cooling, crystals are thoroughly deposited and collected by suction filtration. After washing with cold water three times, the crystals are recrystallized from methanol containing 10% water to give crystals of 2-methyl-5-sulfamoyl-2,3-dihydrobenzofuran-7-carboxylic acid, m.p. 245°–246° C.

The following compounds can be produced in the same procedure as Reference Example above:
2-Methyl-5-methylsulfamoyl-2,3-dihydrobenzofuran-7-carboxylic acid, m.p. 205°–207° C.
2-Methyl-5-ethylsulfamoyl-2,3-dihydrobenzofuran-7-carboxylic acid, m.p. 194°–196° C.
Methyl 2-methyl-5-sulfamoyl-2,3-dihydrobenzofuran-7-carboxylate, m.p. 191°–193° C.
2-Methyl-5-butylsulfamoyl-2,3-dihydrobenzofuran-7-carboxylic acid, m.p. 189°–190° C.
2-Methyl-5-dimethylsulfamoyl-2,3-dihydrobenzofuran-7-carboxylic acid, m.p. 181°–183° C.

The invention will be hereinafter described in more detail with reference to the following Examples, but should not be construed as being limited to them.

EXAMPLE 1

A suspension of 10 g of methyl 2-methyl-5-sulfamoyl-2,3-dihydrobenzofuran-7-carboxylate and 7.0 g of 1-ethyl-2-aminomethylpyrrolidine in 50 ml of diethylene glycol is heated at 120°–130° C. and stirred for 18 hours. The reactant solution is cooled to room temperature and added slowly with stirring to 300–400 ml of water. Under ice-cooling crystals are thoroughly deposited. The crude crystals are collected by suction filtration and washed with cold water. The crude crystals obtained are dried and recrystallized from about 220–230 ml of ethyl acetate by the use of decolorizing charcoal to give crystals of N-(1-ethyl-2-pyrrolidinylmethyl)-2-methyl-5-sulfamoyl-2,3-dihydrobenzofuran-7-carboxamide, m.p. 167°–169° C.

EXAMPLE 2

To a solution of 6 g of (−)-2-methyl-5-sulfamoyl-2,3-dihydrobenzofuran-7-carboxylic acid [[$\alpha$]$_D$= −17.04° (dimethylformamide, c=1)] in a mixed solvent of 55 ml of dimethylformamide and 55 ml of acetone is added 5.9 g of triethylamine and the whole is stirred. The solution is cooled to 15° C., and 2.7 g of ethyl chlorocarbonate is added dropwise for 10 minutes. After stirring at room temperature for 40–45 minutes, 7.5 g of (−)-2-aminomethyl-1-ethylpryrrolidine is added and the reactant is stirred at room temperature for 20 minutes and allowed to stand overnight. Excess triethylamine and acetone are distilled off under diminished pressure and the residue obtained is poured with stirring into 500–600 ml of water. Precipitated crystals are collected by suction filtration, washed with water and dried. The filtrate, aqueous layer is extracted with ethyl acetate three times and the extract layer is washed with water and dried. Ethyl acetate is distilled off under reduced pressure to afford crude crystals. Both the crude crystals are combined and recrystallized from ethyl acetate to give crystals of N-(1-ethyl-2-pyrrolidinylmethyl)-2-methyl-5-sulfamoyl-2,3-dihydrobenzofuran-7-carboxamide, m.p. 155°–156° C., [$\alpha$]$_D$= −64.671° (dimethylformamide, c=1), which is an optically active compound.

EXAMPLE 3

(+)-2-Methyl-5-sulfamoyl-2,3-dihydrobenzofuran-7-carboxylic acid [[$\alpha$]$_D$= +16.67° (dimethylformamide, c=1)], 6 g, is dissolved in a mixed solvent of 55 ml of dimethylformamide and 55 ml of acetone and 5.9 g of triethylamine is added, and the whole is stirred. Under cooling at 15° C. 2.7 g of ethyl chlorocarbonate is added dropwise for 10 minutes and the solution is stirred at room temperature for 40–45 minutes. Then, (−)-1-ethyl-2-aminomethylpyrrolidine, 7.5 g, is added and the reactant is stirred at room temperature for 20 minutes and allowed to stand overnight. Excess triethylamine and acetone are distilled off under reduced pressure and the resulting residue is poured while stirring into 500–600 ml of water. Precipitated cystals are separated by suction filtration, washed with water and dried. The filtrate, aqueous layer is extracted with ethyl acetate three times. The extract layer is washed with water and dried, and ethyl acetate is distilled off under reduced pressure to give crude crystals. Both the crude crystals are put together and recrystallized from ethyl acetate to afford crystals of N-(1-ethyl-2-pyrrolidinylmethyl)-2-methyl-5-sulfamoyl-2,3-dihydrobenzofuran-7-carboxamide, m.p. 164°–165° C., [$\alpha$]$_D$= −50.867° (dimethylformamide, c=1), which is an optically active compound.

EXAMPLE 4

To a solution of 6 g of (−)-2-methyl-5-sulfamoyl-2,3-dihydrobenzofuran-7-carboxylic acid [[$\alpha$]$_D$= −17.04° (dimethylformamide, c=1)] in a mixed solvent of 55 ml of dimethylformamide and 55 ml of acetone is added 5.9 g of triethylamine and the whole is stirred. The system is cooled to 15° C. and 2.7 g of ethyl chlorocarbonate is added dropwise for 10 minutes. After stirring at room temperature for 40–45 minutes, 7.5 g of (+)-2-aminomethyl-1-ethylpyrrolidine is added. The reactant is stirred at room temperature for 20 minutes and allowed to stand overnight. Excess triethylamine and acetone are distilled off under reduced pressure and the residue obtained is poured into 500–600 ml of water while stirring. Precipitated crystals are collected by suction filtration, washed with water and dried. The crude crystals are recrystallized from ethyl acetate to give crystals of N-(1-ethyl-2-pyrrolidinylmethyl)-2-methyl-5-sulfamoyl-2,3-dihydrobenzofuran-7-carboxamide which is an optically active compound and has a m.p. 163°–164° C. and [$\alpha$]$_D$= +50.815° (dimethylformamide, c=1).

EXAMPLE 5

To a solution of 6 g of (+)-2-methyl-5-sulfamoyl-2,3-dihydrobenzofuran-7-carboxylic acid [[$\alpha$]$_D$= +16.67° (dimethylformamide, c=1)] in a mixed solvent of 55 ml of dimethylformamide and 55 ml of acetone is added 8.2 ml of triethylamine and the solution is stirred. Under cooling at 15° C., 2.7 g of ethyl chlorocarbonate is added dropwise for 10 minutes. After stirring at room temperature for 40–45 minutes 7.5 g of (+)-2-aminomethyl-1-ethylpyrrolidine is added, and the reactant is stirred at room temperature for 20 minutes and allowed to stand overnight. Excess triethylamine and acetone are distilled off under diminished pressure and the resulting residue is incorporated while stirring into 500–600 ml of water. Precipitated crystals are collected by suction filtration, washed with water and dried. The crystals are recrystallized from ethyl acetate to give an optically active isomer, crystals of N-(1-ethyl-B 2-pyrrolidinylmethyl)-2-methyl-5-sulfamoyl-2,3-dihydrobenzofuran-7-carboxamide, m.p. 156°–157° C., $[\alpha]_D = +64.648°$ (dimethylformamide, c=1).

EXAMPLE 6

A suspension of 4.0 g of methyl 2-methyl-5-sulfamoyl-2,3-dihydrobenzofuran-7-carboxylate and 3.37 g of 1-benzyl-2-aminomethyl-pyrrolidine in 15 ml of diethylene glycol is heated at 120°–130° C. and stirred for 30–31 hours. The reaction solution is cooled to room temperature, poured into 150–200 ml of water, and extracted with ethyl acetate three times. The ethyl acetate extract is washed with water followed by sodium chloride saturated water. The product is dried over magnesium sulfate and the solvent is distilled off under diminished pressure. The resulting residue is recrystallized from isopropanol by the use of decolorizing charcoal to give crystals of N-(1-benzyl-2-pyrrolidinylmethyl)-2-methyl-5-sulfamoyl-2,3-dihydrobenzofuran-7-carboxamide, m.p. 161°–167° C.

EXAMPLE 7

A suspension of 5.2 g of methyl 2-methyl-5-sulfamoyl-2,3-dihydrobenzofuran-7-carboxylate and 4.5 g of 1-isobutyl-2-aminomethylpyrrolidine in 20 ml of diethylene glycol is heated at 130°–140° C. and stirred for 18–19 hours. The reaction solution is cooled to room temperature and poured into 150–200 ml of water while stirring. Under ice-cooling crystals are deposited thoroughly and collected by suction filtration. The crude crystals are washed with cold water, dissolved in chloroform and separated on a column of silica gel (developing solvent: methanol/chloroform=1/9). Crystals obtained are recrystallized from about 35 ml of methanol to give crystals of N-(1-isobutyl-2-pyrrolidinylmethyl)-2-methyl-5-sulfamoyl-2,3-dihydrobenzofuran-7-carboxamide, m.p. 182°–184° C.

EXAMPLE 8

A suspension of 4.4 g methyl 2-methyl-5-sulfamoyl-2,3-dihydrobenzofuran-7-carboxylate and 3.3 g of 1-butyl-2-aminomethylpyrrolidine in 25 ml of diethylene glycol is heated at 120°–130° C. and stirred for 18–20 hours. The reaction solution is cooled to room temperature and added slowly to 150 ml–200 ml of water while stirring. Under ice-cooling crystals are precipitated thoroughly and collected by suction filtration. The crude crystals are dried and recrystallized from ethyl acetate to give crystals of N-(1-butyl-2-pyrrolidinylmethyl)-2-methyl-5-sulfamoyl-2,3-dihydrobenzofuran-7-carboxamide, m.p. 169.5°–170.5° C.

EXAMPLE 9

2-Methyl-5-methylsulfamoyl-2,3-dihydrobenzofuran-7-carboxylic acid, 5.0 g, is dissolved in a mixed solvent of 50 ml of dimethylformamide and 50 ml of acetone, 5.7 ml of triethylamine is added and the solution is stirred. Under cooling at 15°–18° C. 2.1 g of ethyl chlorocarbonate is added dropwise for 10 minutes. After stirring at room temperature for 40–45 minutes, 3.0 g of 1-ethyl-2-aminomethylpyrrolidine is added. The reactant is stirred at room temperature for 20 minutes and allowed to stand for 15 hours. Then, excess triethylamine and acetone are distilled off, and the resulting residue is poured into 400 ml of water and extracted with ethyl acetate three times. The ethyl acetate extract layer is washed with water and dried and the ethyl acetate is distilled off under reduced pressure. The residue obtained is dissolved in chloroform and hydrochloric acid gas is blown into the solution. Excess hydrochloric acid gas and chloroform are distilled off under diminished pressure. The resulting residue is crystallized from isopropanol/methanol (3/1) to give crystals of N-(1-ethyl-2-pyrrolidinylmethyl)-2-methyl-5-methylsulfamoyl-2,3-dihydrobenzofuran-7-carboxamide hydrochloride, m.p. 202°–205° C.

EXAMPLE 10

2-Methyl-5-methylthio-2,3-dihydrobenzofuran-7-carboxylic acid, 4.6 g, is dissolved in 50 ml of acetone, 6.9 ml of triethylamine is added and the whole is stirred. Under cooling at 10° C. 2.7 g of ethyl chlorocarbonate is added dropwise for 3–5 minutes. After stirring at room temperature for 30 minutes, 3.4 g of 1-ethyl-2-aminomethylpyrrolidine is added and the reactant is stirred at room temperature for 20 minutes and allowed to stand for 15 hours. Then, excess triethylamine and acetone are distilled off under reduced pressure. To the resulting residue is added 50 ml of water, and the solution is extracted three times with ethyl acetate. The ethyl acetate extract layer is washed with sodium bicarbonate saturated aqueous solution, water and sodium chloride saturated water in this sequence, dried and blown into by hydrochloric acid gas. Excess hydrochloric acid gas and ethyl acetate are distilled off under reduced pressure. To the residue are added 60 ml of ethyl acetate and 30 ml of ether to cause crystallization at 0° C. Deposited crude crystals are recrystallized from a mixed solvent of ethyl acetate/isopropanol (100/7) to give crystals of N-(1-ethyl-2-pyrrolidinylmethyl)-2-methyl-5-methylthio-2,3-dihydrobenzofuran-7-carboxamide hydrochloride, m.p. 145°–150° C.

EXAMPLE 11

2-Methyl-5-methylsulfonyl-2,3-dihydrobenzofuran-7-carboxylic acid, 5.0 g, is dissolved in a mixed solvent of 40 ml of dimethylformamide and 20 ml of acetone, 6.5 ml of triethylamine is added, and the whole is stirred. At room temperature, 2.3 g of ethyl chlorocarbonate is added and the solution is stirred for one hour. Thereafter, 3.0 g of 1-ethyl-2-aminomethylpyrrolidine is added, and the reactant is stirred for one and a half hours and allowed to stand for 15 hours. After excess triethylamine and acetone are distilled off under reduced pressure, the residue obtained is poured into 300–400 ml of water and extracted three times with ethyl acetate. The extract layer is washed with aqueous sodium bicarbonate solution and water and dried. The ethyl acetate is distilled off under diminished pressure and the resulting residue is again dissolved in chloroform and hydrochloric acid is blown into the solution. Excess hydrochloric acid gas and chloroform are distilled off under reduced pressure and the resulting residue is dissolved into 35–40 ml of isopropanol and filtered. To the filtrate solution is added 110–120 ml of ethyl acetate and the system is cooled with ice to give crystals of N-(1-ethyl-2-pyrrolidinylmethyl)-2-methyl-5-methylsulfonyl-2,3-dihydrobenzofuran-7-carboxamide hydrochloride, m.p. 186°–189° C.

EXAMPLE 12

To a solution of 5 g of 2-methyl-5-sulfamoyl-2,3-dihydrobenzofuran-7-carboxylic acid in a mixed solvent of 50 ml of dimethylformamide and 50 ml of acetone is added 6.5 ml of triethylamine and the solution is stirred. Under cooling at 15°–18° C. 2.2 g of ethyl chlorocarbonate is added dropwise for 10 minutes and the whole is stirred at room temperature for 40 minutes. Then, 3.3 of 1-propyl-2-aminomethylpyrrolidine is added and the reactant is stirred at room temperature for 40 minutes. After it is allowed to stand for 19 hours, excess triethylamine and acetone are distilled off and the resulting residue is slowly poured into 400 ml of water with stirring. Under ice-cooling, crystals are precipitated thoroughly and collected by suction filtration. The crystals are washed with water and dried. The filtrate, aqueous layer is further extracted with chloroform three times, and the extract chloroform layer is washed with aqueous sodium bicarbonate solution and water and dried. The chloroform is distilled off under reduced pressure and to the residue obtained is added isopropanol. Crystals are deposited and collected by suction filtration. Both the crude crystals are put together and recrystallized from isopropanol/methanol (1/1) to give crystals of N-(1-propyl-2-pyrrolidinylmethyl)-2-methyl-5-sulfamoyl-2,3-dihydrobenzofuran-7-carboxamide, m.p. 177°–180° C.

EXAMPLE 13

2-Methyl-5-sulfamoyl-2,3-dihydrobenzofuran-7-carboxylic acid, 5.0 g, is dissolved in a mixed solvent of 50 ml of dimethylformamide and 50 ml of acetone, 6.5 ml of triethylamine is added and the solution is stirred. Under cooling at 15°–18° C., 2.2 g of ethyl chlorocarbonate is added dropwise for 10 minutes, and the solution is stirred at room temperature for one hour. Thereafter, 2.7 g of 1-methyl-2-aminomethylpyrrolidine is added and the whole is stirred at room temperature for 3 hours and allowed to stand for 15 hours. Excess triethylamine and acetone are distilled off under reduced pressure and the resulting residue is poured into 300–400 ml of water. The aqueous layer is extracted via with chloroform three times and the extract layer is washed with aqueous sodium bicarbonate solution, water and sodium chloride saturated water in this sequence. After drying, the chloroform is distilled off under reduced pressure and the residue obtained is recrystallized from ethyl acetate to give crystals of N-(1-methyl-2-pyrrolidinyl-methyl)-2-methyl-5-sulfamoyl-2,3-dihydrobenzofuran-7-carboxamide, m.p. 187°–189° C.

EXAMPLE 14

A suspension of 5.2 g of 2-methyl-5-sulfamoyl-2,3-dihydrobenzofuran-7-carboxylic acid in 50 ml of thionyl chloride is refluxed and stirred for about 8 hours to give a transparent solution. The reaction solution is cooled to room temperature and excess thionyl chloride is distilled off under diminished pressure. To the residue obtained is added 20 ml of chloroform and the chloroform is distilled off under reduced pressure. The residue is dissolved into 50 ml of chloroform, and 3 g of triethylamine followed by 5.0 g of 4-amino-1-benzylpiperidine is dropwise added with stirring. After stirring at room temperature for 2 hours, the reaction solution is washed with water to deposit crystals. The crystals are collected by suction filtration, washed with water and dried. The filtrate, chloroform layer is separated and dried, and the chloroform is distilled off to separate out crude crystals. Both the crude crystals are combined and recrystallized from a mixed solvent of chloroform/methanol (2/1) to give crystals of N-(1-benzyl-4-piperidinyl)-2-methyl-5-sulfamoyl-2,3-dihydrobenzofuran-7-carboxamide, m.p. 226°–228° C.

The following compounds are prepared in the same procedures as in the Examples above.

15. N-[2-(diethylamino)ethyl]-2-methyl-5-sulfamoyl-2,3-dihydrobenzofuran-7-carboxamide, m.p. 145°–147° C.
16. N-(2-morpholinoethyl)-2-methyl-5-sulfamoyl-2,3-dihydrobenzofuran-7-carboxamide, m.p. 225°–226° C.
17. N-(2-piperidinoethyl)-2-methyl-5-sulfamoyl-2,3-dihydrobenzofuran-7-carboxamide, m.p. 154°–155° C.
18. N-(1-phenethyl-4-piperidinyl)-2-methyl-5-sulfamoyl-2,3-dihydrobenzofuran-7-carboxamide, m.p. 231°–233° C.
19. N-(1-benzyl-3-pyrrolidinylmethyl)-2-methyl-5-sulfamoyl-2,3-dihydrobenzofuran-7-carboxamide, m.p. 163°–165° C.
20. N-(1-benzyl-3-pyrrolidinyl)-2-methyl-5-sulfamoyl-2,3-dihydrobenzofuran-7-carboxamide, m.p. 194°–196° C.
21. N-(1-phenethyl-2-pyrrolidinylmethyl)-2-methyl-5-sulfamoyl-2,3-dihydrobenzofuran-7-carboxamide, m.p. 204°–209° C.
22. N-(1-ethyl-2-pyrrolidinylmethyl)-5-sulfamoyl-2,3-dihydrobenzofuran-7-carboxamide monohydrate, m.p. 189°–190° C.
23. N-(1-benzyl-2-pyrrolidinylmethyl)-5-sulfamoyl-2,3-dihydrobenzofuran-7-carboxamide, m.p. 208°–209° C.
24. N-(1-ethyl-2-pyrrolidinylmethyl)-6-sulfamoylchromene-8-carboxamide, m.p. 179°–181° C.
25. N-(1-ethyl-2-pyrrolidinylmethyl)-2-piperidinomethyl-5-sulfamoyl-2,3-dihydrobenzofuran-7-carboxmide, m.p. 158°–160° C.
26. N-(1-ethyl-2-pyrrolidinylmethyl)-2-phenylthiomethyl-5-sulfamoyl-2,3-dihydrobenzofuran-7-carboxamide hydrochloride, m.p. 229°–231° C.
27. N-(1-allyl-2-pyrrolidinylmethyl)-2-methyl-5-sulfamoyl-2,3-dihydrobenzofuran-7-carboxamide, m.p. 167°–168° C.
28. N-(1-propargyl-2-pyrrolidinylmethyl)-2-methyl-5-sulfamoyl-2,3-dihydrobenzofuran-7-carboxamide
29. N-(1-p-fluorobenzyl-2-pyrrolidinylmethyl)-2-methyl-5-sulfamoyl-2,3-dihydrobenzofuran-7-carboxamide, m.p. 133°–135° C.
30. N-(1-ethyl-2-pyrrolidinylmethyl)-2-methyl-5-dimethylsulfamoyl-2,3-dihydrobenzofuran-7-carboxamide hydrochloride. 0.1 isopropanol adduct, m.p. 109°–111° C.
31. N-(1-ethyl-2-pyrrolidinylmethyl)-2-methyl-5-ethylsulfamoyl-2,3-dihydrobenzofuran-7-carboxamide hydrochloride, m.p. 102°–105° C.
32. N-(1-ethyl-2-pyrrolidinylmethyl)-2-methyl-5-butylsulfamoyl-2,3-dihydrobenzofuran-7-carboxamide hydrochloride, m.p. 150°–152° C.
33. N-(1-ethyl-2-pyrrolidinylmethyl)-2-methyl-5-methylsulfinyl-2,3-dihydrobenzofuran-7-carboxamide, m.p. 131°–134° C.
34. N-(1-ethyl-2-pyrrolidinylmethyl)-N,2-dimethyl-5-sulfamoyl-2,3-dihydrobenzofuran-7-carboxamide, m.p. 148°–150° C.

35. N-(1-ethyl-2-pyrrolidinylmethyl)-2-methyl-4-amino-5-sulfamoyl-2,3-dihydrobenzofuran-7-carboxamide
36. N-(1-ethyl-2-pyrrolidinylmethyl)-2-methyl-4-chloro-5-sulfamoyl-2,3-dihydrobenzofuran-7-carboxamide
37. N-(1-ethyl-2-pyrrolidinylmethyl)-2-bromomethyl-5-sulfamoyl-2,3-dihydrobenzofuran-7-carboxamide
38. N-(1-methyl-2-pyrrolidinylmethyl)-2-methyl-5-methylsulfamoyl-2,3-dihydrobenzofuran-7-carboxamide, m.p. 132°–135° C.
39. N-(1-propyl-2-pyrrolidinylmethyl)-2-methyl-5-methylsulfamoyl-2,3-dihydrobenzofuran-7-carboxamide, m.p. 141°–143° C.
40. N-(1-isopropyl-2-pyrrolidinylmethyl)-2-methyl-5-methylsulfamoyl-2,3-dihydrobenzofuran-7-carboxamide, m.p. 144°–147° C.
41. N-(1-isobutyl-2-pyrrolidinylmethyl)-2-methyl-5-methylsulfamoyl-2,3-dihydrobenzofuran-7-carboxamide hydrochloride, m.p. 168°–172° C.
42. N-(1-benzyl-2-pyrrolidinylmethyl)-2-methyl-5-methylthio-2,3-dihydrobenzofuran-7-carboxamide fumarate, m.p. 118°–120° C.
43. N-(1-propyl-2-pyrrolidinylmethyl)-2-methyl-5-methylsulfonyl-2,3-dihydrobenzofuran-7-carboxamide hydrochloride, m.p. 215°–217° C.
44. N-(1-isobutyl-2-pyrrolidinylmethyl)-2-methyl-5-methylsulfonyl-2,3-dihydrobenzofuran-7-carboxamide hydrochloride.0.5 hydrate, m.p. 177°–181° C.
45. N-(1-ethyl-2-pyrrolidinylmethyl)-2-dimethylaminomethyl-5-sulfamoyl-2,3-dihydrobenzofuran-7-carboxamide, m.p. 152°–153° C.
46. N-(1-p-chlorobenzyl-2-pyrrolidinylmethyl)-2-methyl-5-sulfamoyl-2,3-dihydrobenzofuran-7-carboxamide, m.p. 167°–169° C.
47. N-(1-isobutyl-2-pyrrolidinylmethyl)-5-sulfamoyl-2,3-dihydrobenzofuran-7-carboxamide
48. N-(1-cyclohexyl-2-pyrrolidinylmethyl)-2-methyl-5-sulfamoyl-2,3-dihydrobenzofuran-7-carboxamide, m.p. 183°–184° C.
49. N-(1-propyl-2-pyrrolidinylmethyl)-2-methyl-5-methylthio-2,3-dihydrobenzofuran-7-carboxamide fumarate, m.p. 160°–162° C.
50. N-(1-propyl-2-pyrrolidinylmethyl)-2-methyl-5-methylsulfinyl-2,3-dihydrobenzofuran-7-carboxamide, m.p. 143°–145° C.

We claim:

1. Compounds of the formula:

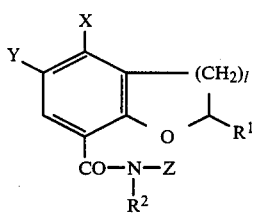

wherein l is 1 or 2; X is hydrogen atom, amino group or halogen atom; Y is —S(O)$_m$—R$^3$ wherein R$^3$ is lower alkyl group and m is 0, 1 or 2, or

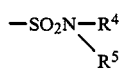

wherein R$^4$ and R$^5$ are the same or different and each is hydrogen atom or lower alkyl group; R$^1$ is hydrogen atom, lower alkyl group, arylthiomethyl group, halogenomethyl group or

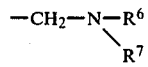

wherein R$^6$ and R$^7$ are the same or different and each is hydrogen atom or lower alkyl group or R$^6$ and R$^7$ form, together with the adjacent nitrogen atom, a heterocycle selected from the group consisting of pyrrolidine, piperidine and morpholine; R$^2$ is hydrogen atom or lower alkyl group; and Z is

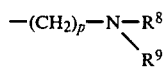

wherein p is 2 or 3, R$^8$ and R$^9$ are the same or different and each is lower alkyl group or R$^8$ and R$^9$ form, together with the adjacent nitrogen atom, a heterocycle selected from the group consisting of pyrrolidine, piperidine and morpholine, or

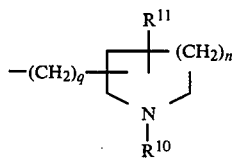

wherein q is 0 or 1, n is 1 or 2, R$^{10}$ is lower alkyl group, lower alkenyl group, lower alkynyl group, phenyl(lower)alkyl group or cycloalkyl group and R$^{11}$ is hydrogen atom or lower alkyl group, physiologically acceptable salts thereof or optical isomers thereof.

2. A compound according to claim 1: N-(1-ethyl-2-pyrrolidinylmethyl)-2-methyl-5-sulfamoyl-2,3-dihydrobenzofuran-7-carboxamide.

3. A compound according to claim 1: N-(1-benzyl-2-pyrrolidinylmethyl)-2-methyl-5-sulfamoyl-2,3-dihydrobenzofuran-7-carboxamide.

4. A compound according to claim 1: N-(1-isobutyl-2-pyrrolidinylmethyl)-2-methyl-5-sulfamoyl-2,3-dihydrobenzofuran-7-carboxamide.

5. A compound according to claim 1: N-(1-butyl-2-pyrrolidinylmethyl)-2-methyl-5-sulfamoyl-2,3-dihydrobenzofuran-7-carboxamide.

6. A compound according to claim 1: N-(1-ethyl-2-pyrrolidinylmethyl)-2-methyl-5-methylthio-2,3-dihydrobenzofuran-7-carboxamide hydrochloride.

7. A compound according to claim 1: N-(1-ethyl-2-pyrrolidinylmethyl)-2-methyl-5-methylsulfamoyl-2,3-dihydrobenzofuran-7-carboxamide hydrochloride.

8. A compound according to claim 1: N-(1-ethyl-2-pyrrolidinylmethyl)-2-methyl-5-methylsulfinyl-2,3-dihydrobenzofuran-7-carboxamide.

9. A compound according to claim 1: N-(1-propyl-2-pyrrolidinylmethyl)-2-methyl-5-methylsulfonyl-2,3-dihydrobenzofuran-7-carboxamide hydrochloride.

10. A compound according to claim 1: N-(1-isobutyl-2-pyrrolidinylmethyl)-2-methyl-5-methylsulfonyl-2,3-dihydrobenzofuran-7-carboxamide hydrochloride.½ hydrate.

11. A pharmaceutical composition comprising a psychosomatic-treating effective amount of the compound of claim 1 and a pharmaceutically acceptable carrier.

* * * * *